(12) United States Patent
Ward et al.

(10) Patent No.: US 8,183,540 B2
(45) Date of Patent: May 22, 2012

(54) DROPLET DEFORMATION (75) Inventors: Andrew David Ward, Andover (GB);
Colin David Bain, Durham (GB);
Christopher Daniel Mellor, London (GB)

(73) Assignee: The Science and Technology Facilities Council, Oxfordshire (GB)

( * ) Notice: Subject to any disclaimer, the term of this patent is extended or adjusted under 35 U.S.C. 154(b) by 475 days.

(21) Appl. No.: 12/223,186

(22) PCT Filed: Jan. 25, 2007

(86) PCT No.: PCT/GB2007/000282
§ 371 (c)(1),
(2), (4) Date: Jul. 24, 2008

(87) PCT Pub. No.: WO2007/085854
PCT Pub. Date: Aug. 2, 2007

(65) Prior Publication Data
US 2010/0258964 A1    Oct. 14, 2010

(30) Foreign Application Priority Data
Jan. 25, 2006 (GB) .................................. 0601503.6

(51) Int. Cl.
G01N 21/00 (2006.01)
G01N 23/00 (2006.01)
G02B 5/18 (2006.01)
C08J 7/18 (2006.01)
C08J 3/28 (2006.01)
C08F 2/46 (2006.01)

(52) U.S. Cl. .................... 250/432 R; 250/428; 250/251; 522/1; 522/2; 522/3; 359/566; 359/558; 359/567

(58) Field of Classification Search .................. 250/251, 250/423 R, 428, 432; 522/1, 2, 3; 359/566, 359/558.567
See application file for complete search history.

(56) References Cited

U.S. PATENT DOCUMENTS

| 5,308,976 | A  | * | 5/1994  | Misawa et al. ............... 250/251 |
| 6,639,208 | B2 | * | 10/2003 | Grier et al. .................... 250/251 |
| 6,847,032 | B2 | * | 1/2005  | Grier et al. .................... 250/251 |
| 2002/0185592 | A1 | | 12/2002 | Grier et al. |

FOREIGN PATENT DOCUMENTS

| EP | 1 469 483 A2 | 10/2004 |
| JP | 4-248985 | 9/1992 |
| JP | 11-218691 | 8/1999 |
| WO | WO-99/44488 A3 | 9/1999 |

OTHER PUBLICATIONS

W. Singer et al. Combined optical tweezers and optical stretcher in microscopy. Proceedings of SPIE vol. 4434 (2001). pp. 227-232.*
Urlaub et al. Raman investigation of stryene polymerization in single optically trapped emulsion particles. Chemical Physics Letters 231 (1994), pp. 511-514.*
Bronkhorst et al., Biophysical Journal, vol. 69, pp. 1666-1673, 1995.
Guck et al., Physical Review Letters, vol. 84, No. 23, pp. 5451-5454, 2000.
Dufresne et al., Review of Scientific Instruments, vol. 69, No. 5, pp. 1974-1977, 1998.
Guilford et al., Analytical Biochemistry, vol. 326, pp. 153-166, 2004.
Encinas et al., Langmuir, vol. 14, pp. 5691-5694, 1998.
Ward et al., Chem. Commun., pp. 4515-4517, 2006.
Cojoc et al., "Multiple optical tweezers for micro Raman spectroscopy," Proceedings of the SPIE—The International Society for Optical Engineering, vol. 5930, No. 1, 2005, pp. 1-11.
Buajarern et al., "Controlling and Characterizing the Coagulation of Liquid Aerosol Droplets," Journal of Chemical Physics, vol. 125, No. 11, 2006, pp. 114506/1-114506-10.
Singer et al., "Combined optical tweezers and optical stretcher in microscopy," Proceedings of the SPIE—The International Society for Optical Engineering, vol. 4434, 2001, pp. 227-232.

* cited by examiner

*Primary Examiner* — Sanza McClendon
(74) *Attorney, Agent, or Firm* — Birch, Stewart, Kolasch & Birch, LLP (57) ABSTRACT A technique for shaping droplets is disclosed. Multiple optical traps, or at least one variable geometry trap, are used to deform a droplet. The surface tension of the droplet is lowered to be comparable with the force which can be applied using the optical traps, for example by using a surfactant such as Aerosol OT, with heptane droplets in a solution of sodium chloride. Solidification of deformed droplets can be achieved using polymerization.

38 Claims, 8 Drawing Sheets

Cleave

DROPLET DEFORMATION

CROSS-REFERENCE TO RELATED APPLICATIONS

This application is a U.S. national stage filing under 35 U.S.C. §371 of PCT Application No. PCT/GB2007/000282 filed on 25 Jan. 2007, currently pending, which claims foreign priority to GB0601503.6, filed 25 Jan. 2006.

INTRODUCTION

The present invention relates to method and apparatus for deforming droplets, for example microscopic droplets in an emulsion, and also to methods and apparatus for forming correspondingly shaped particles.

DISCUSSION OF THE PRIOR ART

There are many applications where microscopic particles and structures having particular shapes and properties are required. For example, Micro-electromechanical systems (MEMS), surface coatings, photonic waveguides etc. The manufacture of such microscopic particles is difficult and expensive.

Colloidal structures which are particularly important in the paint and food industries are also studied using very small scale technologies. The control of particle morphology in these applications is limited to particles and spherical droplets.

Moreover, in the field of photonics, surface coatings are often essential to the properties of light carrying structures. Certain features within these device can be very difficult manufacture.

A current method of manufacturing microscopic parts is the SU8 process. This begins with a gel block which is hardened to form a shaped object. The hardening/shaping process can be achieved by many methods including irradiating with laser light. Once irradiated the gel solidifies and any regions not irradiated can be removed to form the desired shape.

The present invention seeks to provide an improved method of fabricating very small scale or microscopic particles and devices.

The present invention also provides a method of deforming droplets that may be useful in a variety of applications.

SUMMARY OF THE INVENTION

Accordingly, the invention provides a method of shaping a droplet by varying the geometry and/or positions of one or more optical traps directed at the droplet. In particular, there is provided a method of shaping a droplet comprising: generating a plurality of optical traps focussed on the droplet; and manipulating the optical traps to change the shape of the droplet. The optical traps are translated in controlled directions to change the shape of the droplet.

Alternatively or in combination with the above method, a droplet may be deformed by the following method: generating at least one variable geometry optical trap; directing the at least one variable geometry optical trap at the droplet; and adjusting the geometry of the optical trap to deform the droplet.

The droplet may typically comprise or be formed of a first fluid, suspended directly within a second, surrounding fluid. The first and second fluids will therefore typically be immiscible, and may form at least part of an emulsion system such as an oil-in-water based emulsion. However, other systems may also be used, for example, the method could be used to change the shape of a bead, such as a bead of a gel or other flexible material suspended in a surrounding medium.

A surfactant may be added or used to lower the surface tension between the droplet and the fluid around the droplet, for example by including in the above mentioned emulsion system. Preferably, the interfacial tension between the droplet and surrounding fluid is arranged to be less than about $10^{-4}$ $Nm^{-1}$, and more preferably below about $10^{-5}$ $Nm^{-1}$, because optical trap forces are typically around $10^{-5}$ to $10^{-6}$ $Nm^{-1}$. Typical oil-water interfacial tensions, without using a surfactant, are around 0.05 $Nm^{-1}$.

The optical traps may be focussed to be incident within the droplet. However, the droplet may also be shaped if the optical traps are incident outside the droplet in the surrounding medium adjacent to the droplet, thereby exerting a force on the adjacent medium to change the shape of the droplet.

Accordingly, the invention also provides a method of forming a shaped droplet, comprising: providing a droplet of a first fluid suspended within a second fluid, along with a surfactant acting to reduce the surface tension at the interface between the droplet and the surrounding second fluid, forming a plurality of optical traps (or one or more variable geometry traps) at the droplet; and moving the optical traps (or varying trap geometry) to deform the droplet.

The invention also provides a droplet (or bead) deformation apparatus comprising: a sample space for holding at least one droplet suspended in a fluid; a trap generator arranged to generate a plurality of optical traps directed at the droplet; and a controller arranged to manipulate the optical traps to change the shape of the droplet.

The apparatus may further comprise at least two cameras for imaging the droplet from at least two aspects. These aspects may be arranged orthogonally, or in any other way so as to provide images showing the three-dimensional shape of the droplet.

The invention also provides a method of making a polymer particle shaped by optical tweezers, comprising: generating a plurality of optical traps directed at a droplet containing monomers; translating the optical traps to shape the droplet; and initiating polymerisation of the droplet.

The droplet may be suspended in an emulsion also containing an initiator. The initiator may be a photo-initiator.

BRIEF DESCRIPTION OF THE DRAWINGS

Embodiments of the invention will now be described, by way of example only, with reference to the accompanying drawings of which.

DETAILED DESCRIPTION OF THE PREFERRED EMBODIMENTS

Figure 1:
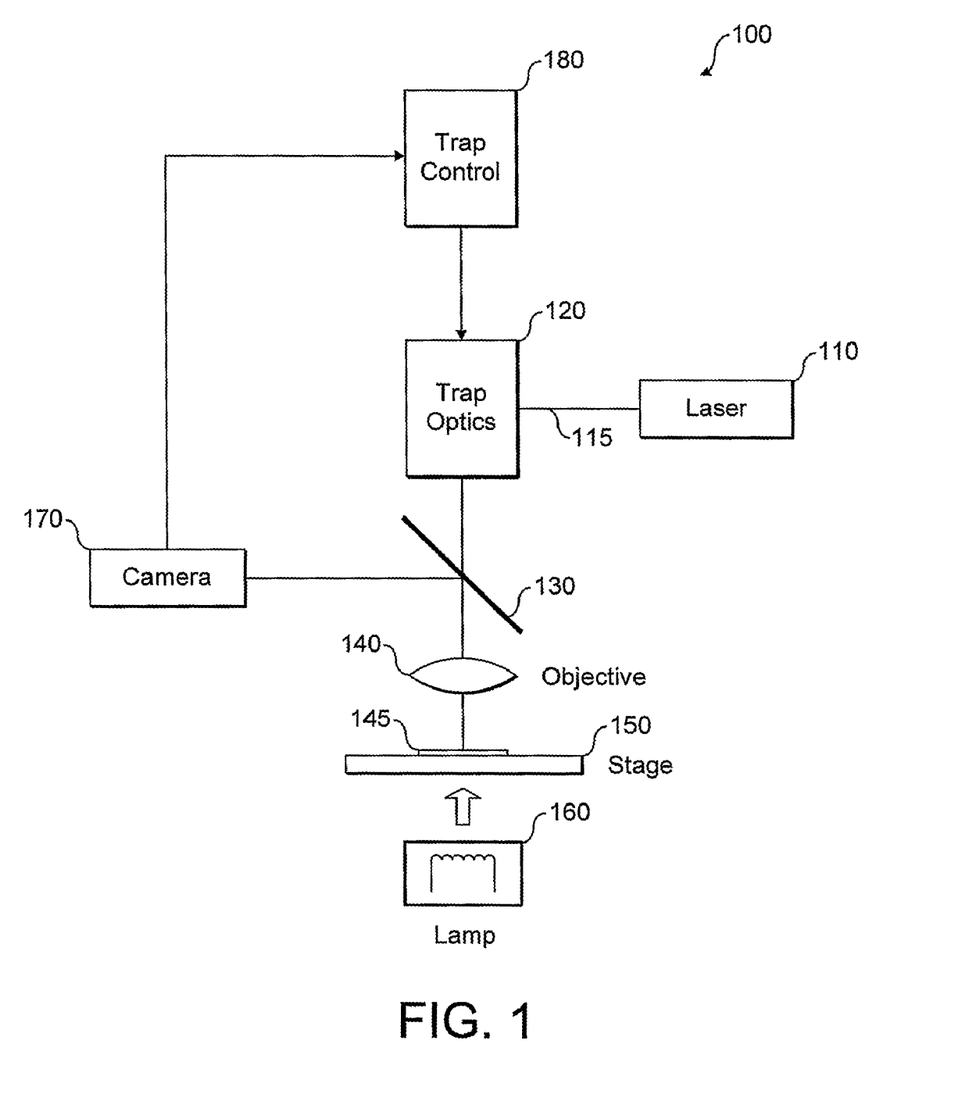
FIG. 1 is a representation of an optical tweezer generation and sample monitoring system of the prior art.

FIG. 1 shows a typical system 100 for generating optical traps. The system 100 includes a laser 110 which supplies a high intensity beam 115 to the trap optics 120. The trap optics convert the beam into multiple beams, if required, and process the beam(s) in manner suitable for producing an optical trap. Typically, the conversion into multiple beams is performed using acousto-optic deflectors (AODs) which temporally divide the light into the required number of beams. The beam or beams output from the trap optics then pass through a beamsplitter 130 and are focussed by a microscope objective or other high NA lens 140. In the focal plane of the beams a sample stage 150 is provided, such that the trapping region of each beam is formed near the top surface of the sample stage. A sample 145 is placed on the stage 150. A lamp 160 illuminates the sample for viewing.

Optionally, a camera (170) and imaging system (which may include parts of the optical system already described) can be used to provide feedback to a trap control (180) to adjust the position of the traps.

Specifically, the laser is a Nd:YAG operating at 1064 nm and commonly lasers operating in the infra-red are used, although other wavelengths may be used. The effectiveness of other wavelengths will depend on the optical properties of the object to be constrained in the optical trap. The beam output power from the trap optics is around 30 mW. The microscope objective has a numerical aperture of 1.2 and a 63× magnification.

However, as will be appreciated by the person skilled in the art, the method and apparatus described above is by way of an example. There are many other techniques for generating multiple beams. The laser and microscope characteristics are also examples and different devices may be used.

The technique of creating optical traps is described in detail in "Creating Multiple Time-Shared Laser Traps with Simultaneous Displacement Detection Using Digital Signal Processing Hardware", Analytical Biochemistry 326, 153 (2004), Guildford et al.

Figure 2A:
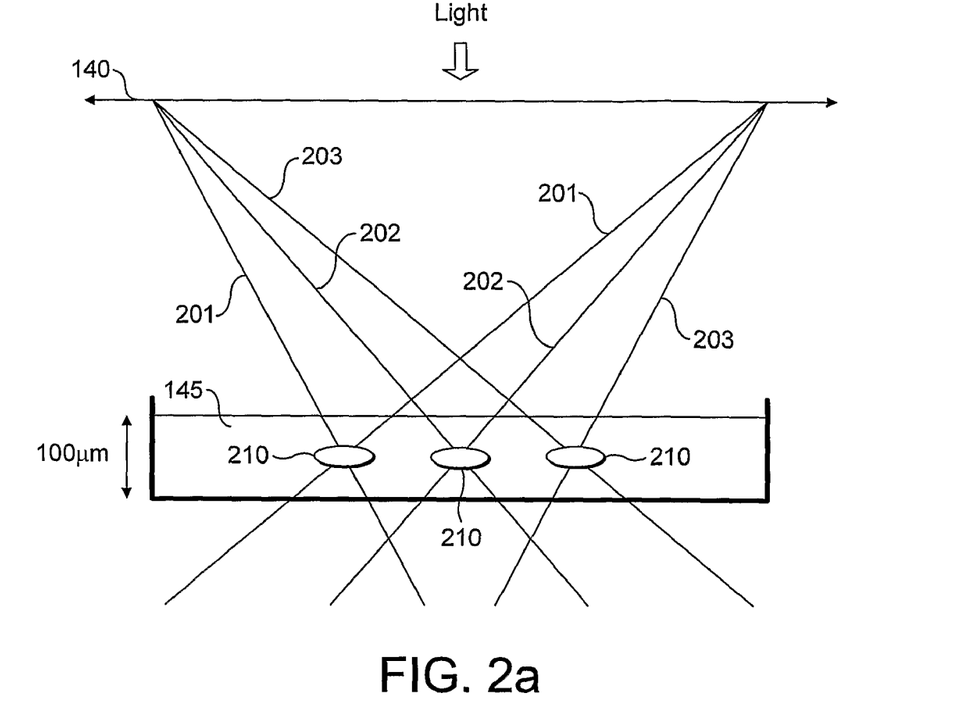
FIG. 2a illustrates the technique of the prior art of directing multiple optical traps in a sample.
Figure 2B:
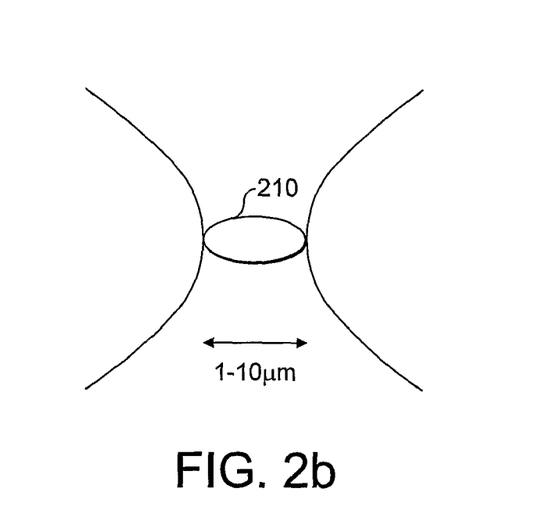
FIG. 2b illustrates the shape of a beam waist of an optical trap of FIG. 2.

FIG. 2a illustrates schematically one way in which multiple traps generated using the set up of FIG. 2 can be directed at the sample 145. The figure shows the microscope objective 140 with three beams incident on the sample. The edges of the beams (which may be considered to be the $1/e^2$ intensity levels) are represented by straight lines. Beam 1 is represented by lines 201, beam 2 is represented by lines 202, and beam 3 is represented by lines 203. Of course, contrary to the schematic representation of the figure, the diameter of the beams at the waist is finite as represented in FIG. 2b. Typically beam waists and optical traps are in the order of 0.2-10 μm. The schematic illustration in FIG. 2a shows how multiple beams may be arranged through a single objective and provide beam waists and hence optical traps 210 in the sample plane.

Typically, optical traps are used to manipulate particles up to around 10 μm in diameter, although particles may sometimes be larger than this. Optical traps to manipulate particles are often called optical tweezers.

Optical tweezers may also be used on specialised emulsion systems to deform the shape of droplets within that emulsion system.

The sample 145 of FIG. 1 may consist of a shallow bath of emulsion. This is placed on the sample stage 150. Typically, the emulsion system consists of heptane droplets suspended in a sodium chloride solution (typically 0.05 M). The bath may contain a 100 μm deep bath of emulsion.

Normally, the interfacial tension between the oil and water is around 1000× the magnitude of any force that may be provided by optical tweezers. However, the surface tension between the two species may be reduced by adding a surfactant to the emulsion. For example, the surfactant Aerosol OT may be used, with a region of ultra low interfacial tension ($<3\times10^{-6}$ Nm$^{-1}$) being found around 20~23° C., in the presence of the NaCl salt.

Figure 3:
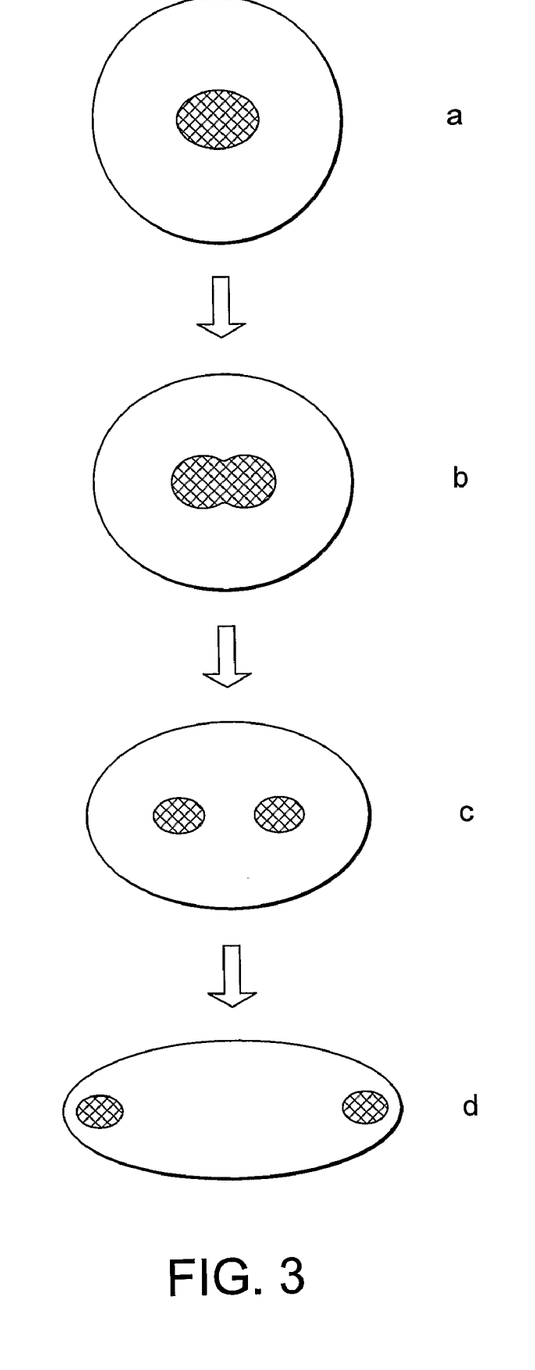
FIG. 3 (a)-(d) shows the stretching of a droplet using two optical traps.

FIG. 3 shows two optical traps incident on an oil droplet suspended in the described solution of sample 145. In FIG. 3a the two optical traps are directed to the same position within the droplet and trap the droplet at that point. In FIG. 3b the two traps have been moved in opposing directions. However, they are still positioned so closely that the traps are overlapping, and little deformation of the droplet will occur. Moving to FIG. 3c the two traps are incident on separate regions of the droplet and are beginning to deform the droplet shape. In FIG. 3d the traps are at the edges of the droplet providing a force to stretch out the droplet resulting in the droplet having an elongated shape.

Figure 4:
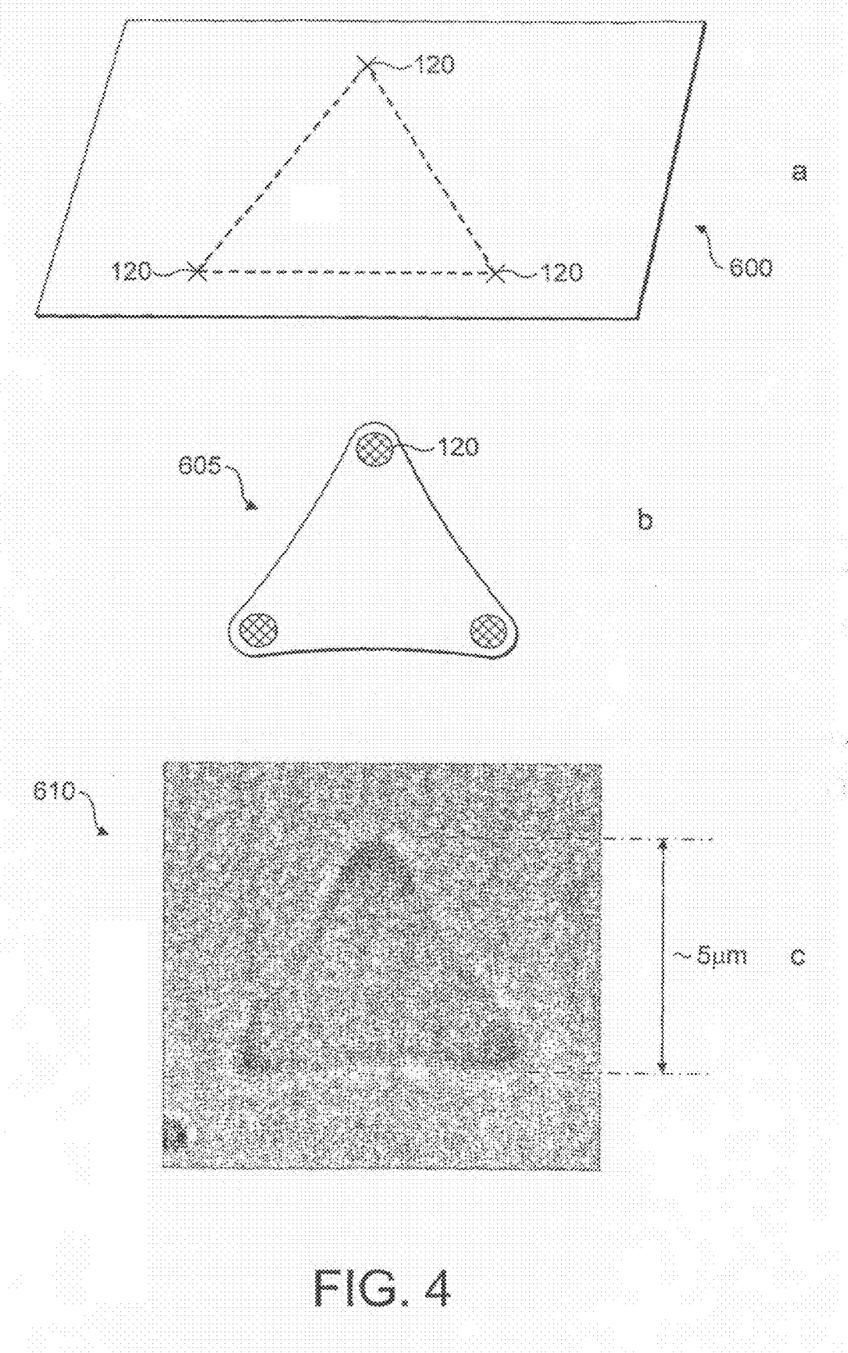
FIG. 4 (a)-(c) illustrates the deformation of a droplet into a triangle using three optical traps.

By increasing the number of optical traps incident on a droplet the complexity of the droplet shape can be increased. FIG. 4 shows a droplet that has been stretched using three optical traps to produce a triangular shaped droplet. As described above in relation to FIG. 3 the droplet is stretched by moving the optical traps away from each other. To produce an equilateral triangle shaped droplet the direction of movement of the traps is 120° apart. The traps start and move within a single plane. FIGS. 4a and 4b show the final positions of the optical traps 120. In particular, an optical trap is positioned near each apex of the triangle (FIG. 4b). FIG. 4c shows a photograph 610 of a triangular droplet that has been produced by the above-described method. The starting droplet diameter is around 5 μm but deformation of droplets in the range 2 to 10 μm has also been demonstrated. The volume of a deformed droplet is unchanged compared to the volume of the original droplet. In FIG. 4c it can also be seen that surface tension causes the sides of the triangle to curve in slightly.

Figure 5:
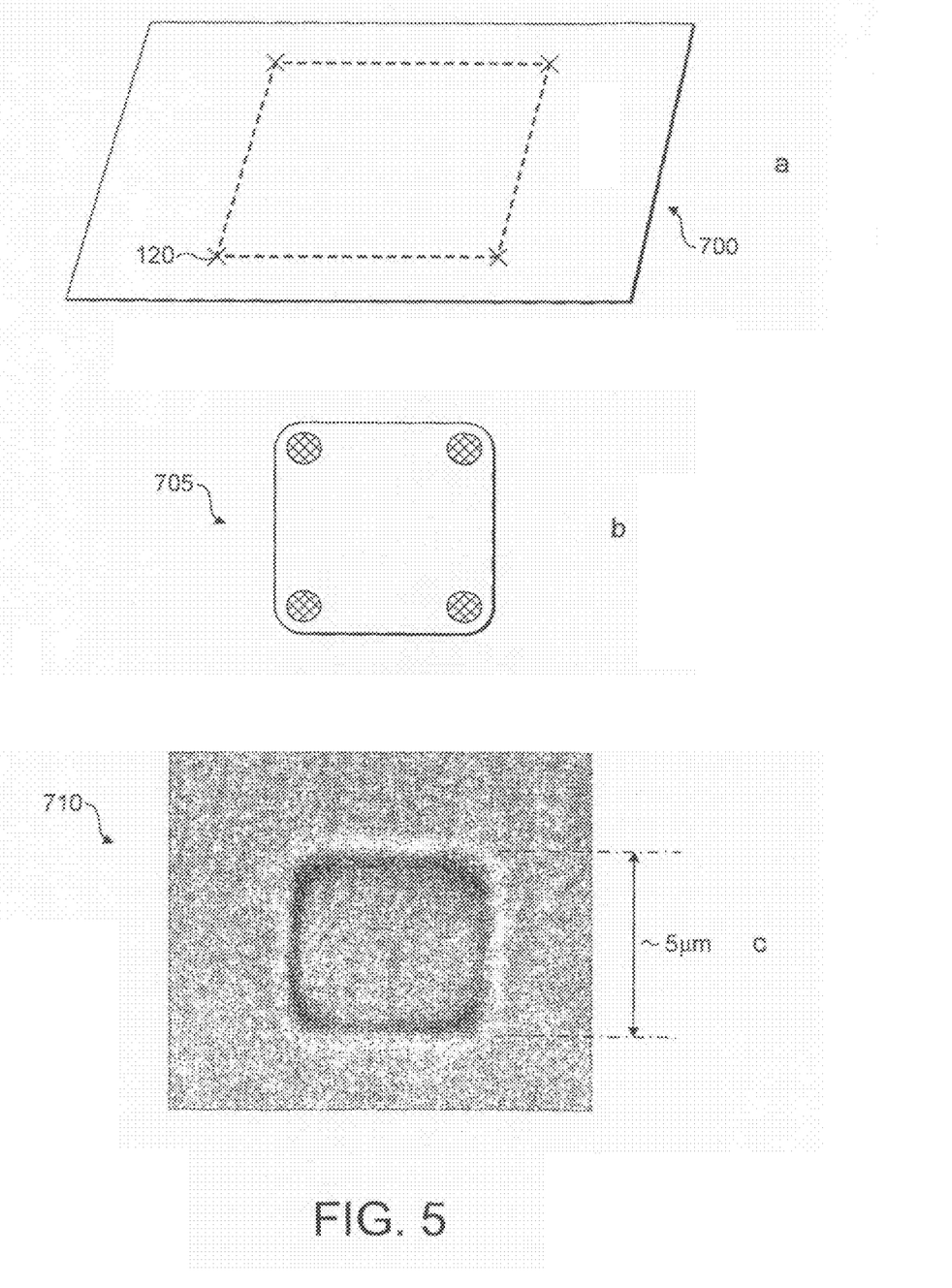
FIG. 5 (a)-(c) illustrates the deformation of a droplet into a square using four optical traps.

The above method can be extended to four optical traps to produce a square, trapezoid or rhombus shaped droplet. FIG. 5 shows a square droplet produced by four traps 120 in a single plane 700. FIG. 5c shows a photograph 710 of a 5 μm square droplet that has been produced.

The above method may be extended by the use of more traps to produce even more detailed and complex shapes. However, as the complexity of the shape increase the demands on the ultra low surface tension requirements of the emulsion increase.

Figure 6:
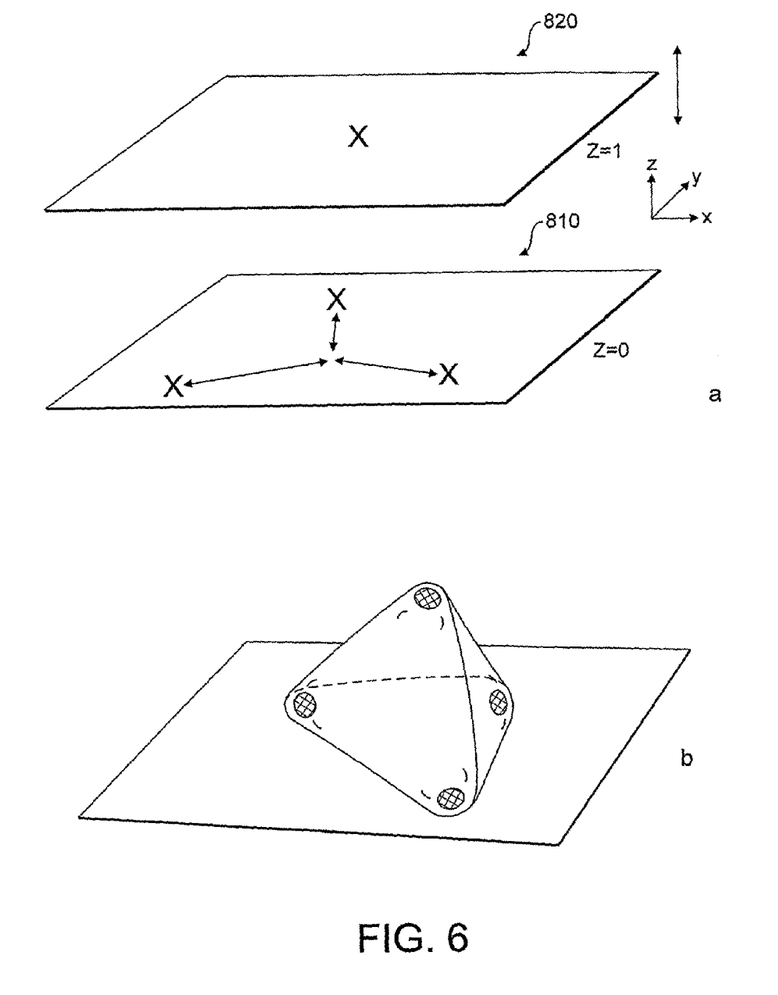
FIG. 6 (a)-(b) illustrates how four optical traps are used to deform a droplet in three dimensions to produce a tetrahedron.

The droplets shown in FIGS. 4c and 5c are deformed by moving optical traps within a single plane. Nevertheless, the droplet is a 3-dimensional body and the technique can be further extended to produce droplets deformed in three dimensions, for example, producing tetrahedrons or cubes. This extension of the technique requires optical traps to apply forces in directions out of single plane. For example, FIG. 6 shows the location of optical traps to produce a tetrahedral droplet. The main difference between deforming the droplet into a tetrahedron and the two-dimensional shapes described above is the need to produce an optical trap in a second plane to provide depth to the droplet shape deformation.

Apparatus suitable for three-dimensional deformation may be similar to that described in relation to FIG. 1. Additionally, the laser beam may be split into two separate beams. The first beam may be directed to the standard trap optics 120 and the AODs, as mentioned above, to produce the traps in the first plane. FIG. 6 shows traps located in two planes, Z=0 and Z=1. The traps in the first plane 810 are identical to those in FIG. 4 and can be moved in the x,y directions (i.e. within the plane) to deform the base of the droplet. The second beam forms a trap 820 the position of which is controlled in a z-direction, out of the x,y sample plane. Stretching of the droplet in the z direction is achieved by translation of the position of the optical trap produced by the second beam. This translation in the z-direction may be achieved by translating the position of the final beam expansion lens in the optical system. A limited amount of movement would be required as the focal point of the beam and hence the optical trap would need around 4-10 µm of movement. As shown in FIG. 6 the final arrangement of traps in three dimensional space will be a fixed apex above a base of three traps. FIGS. 6a and 6b show a tetrahedron produced with three traps in a first plane (Z=0) and a single trap (Z=1) in a second plane.

Clearly the technique may be extended to produce many different shaped droplets by using more optical traps arranged in a plurality of different planes.

Figure 7:
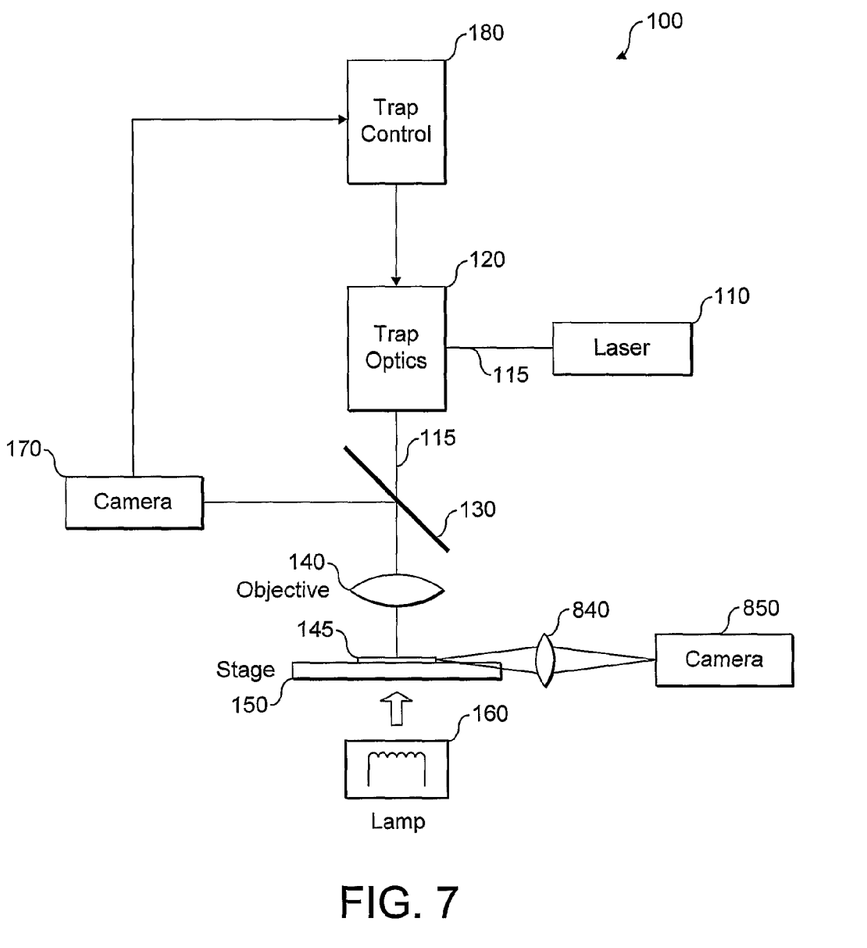
FIG. 7 shows apparatus for viewing the shaped droplet from a side elevation.

The apparatus shown in FIG. 1 only allows the droplet to be viewed from above. Any deformations to the droplet orthogonal to this viewing plane will be difficult to see. In the apparatus of FIG. 7 an additional lens 840 and camera 850 are provided. The lens 840 is a long working distance microscope objective. In this case a 20× magnification is used. The lens 840 is located in the plane of the sample and collects light deflected by the droplet. The light collected by the droplet can then be viewed using the camera 850 to provide side elevation image of the droplet. This extra direction of viewing is desirable when deforming droplets in three dimensions.

The above method of deforming droplets is not limited to forming droplets having two, three or four apexes, but can be extended to use any number of optical traps in many different planes to produce a wide variety of shaped droplets.

In the above described embodiments the optical traps in the Z=0 plane are incident normal to the plane of the sample. However, the method is not limited to such an arrangement. The traps in the Z=0, Z=1 or any other planes may be incident on the sample from other directions.

The emulsion-surfactant system described above is exemplary and many other emulsion-surfactant systems may be used not limited to oil and aqueous solutions. For example, gel droplets may be trapped in a liquid.

Moreover, although in the above described embodiments the optical traps are incident within the droplet, by changing the emulsion system, the optical traps could be incident in the solution just outside the droplet and squeeze the droplet from outside.

In a variation of the above described embodiments, multiple optical traps may be generated using diffractive optical elements (DOEs), spatial light modulators (SLMs), or other techniques. Such devices typically, use an addressable holographic element to divide one laser beam into multiple beams using diffraction. These techniques divide the light spatially, rather than temporally using AODs as described in the embodiment above. The DOEs can be addressed at video rates which allows multiple traps to be created and moved rapidly and easily. This techniques is sometimes known as Dynamic Holographic Optical Tweezers, and more information can be found in "Optical tweezer arrays and optical substrates created with diffractive optical elements", E. R. Dufresne and D. G. Grier, Rev. Sci. Instr. 69, 1974-1977 (1998).

In a further variation, diffractive optical elements, or other techniques, are used to generate multiple beams to produce a single optical trap of controllable geometry. The separate beams are manipulated to change the shape of the trap and hence the shape of a droplet held within the trap. Of course, a combination of any of the techniques described herein may also be used.

The above described droplet deformation technique can be extended to produce a range of shaped particles, for example, by using a controlled process of polymerisation of monomers in the droplet. A compatible initiator may also be included in the emulsion formulation.

Again, the emulsion system may use heptane, Aerosol OT and sodium chloride solution. Added to the system are the monomers and an initiator. A suitable monomer is styrene which is initiated by using dibenzyl-ketone (DBK). An alternative monomer may be methyl methacrylate which is initiated using 2,2'-azobis(2-isobutyronitrile) (AIBN). These initiators are oil-soluble and will therefore reside in the droplet. Alternatively, a water-soluble initiator such as 2,2'-azobis(2-amidinopropane) may be used. However, this will reside outside the droplet and is likely to be less effective than an initiator located inside the droplet.

The above initiators are activated by the action of light of a particular wavelength (photo-initiators). For DBK and ABAP a wavelength of 313 nm is used to initiate the polymerisation process. For AIBP a wavelength of 366 nm is used. Generally, UV wavelengths in the range 300-370 nm are used with photo-initiators to start polymerisation.

Another polymer-initiator system that may be used is an acrylate based system (e.g. isobornyl acrylate and dipentaerythritol pentacrylate) for which the photo-initiator is 2-benzyl-2-dimethylamino-1-(4-morpholinophenyl)-butan-1-one.

Alternatively, initiators activated by heat, radiation, ultrasound or other means may be used.

Polymerisation of the deformed droplets described above preferably occurs rapidly to avoid loss of shape of the droplet. Depending on the formulations used, the interfacial tension at the droplet surface may increase significantly during polymerisation. Therefore, if the polymerization process takes place slowly, the balance between the laser trapping force and the interfacial tension may result in the droplet attempting to revert to a sphere. This problem can also be overcome by causing polymerization in the core of the droplet before the surface so that the low interfacial tension is maintained for as long as possible.

Figure 8:
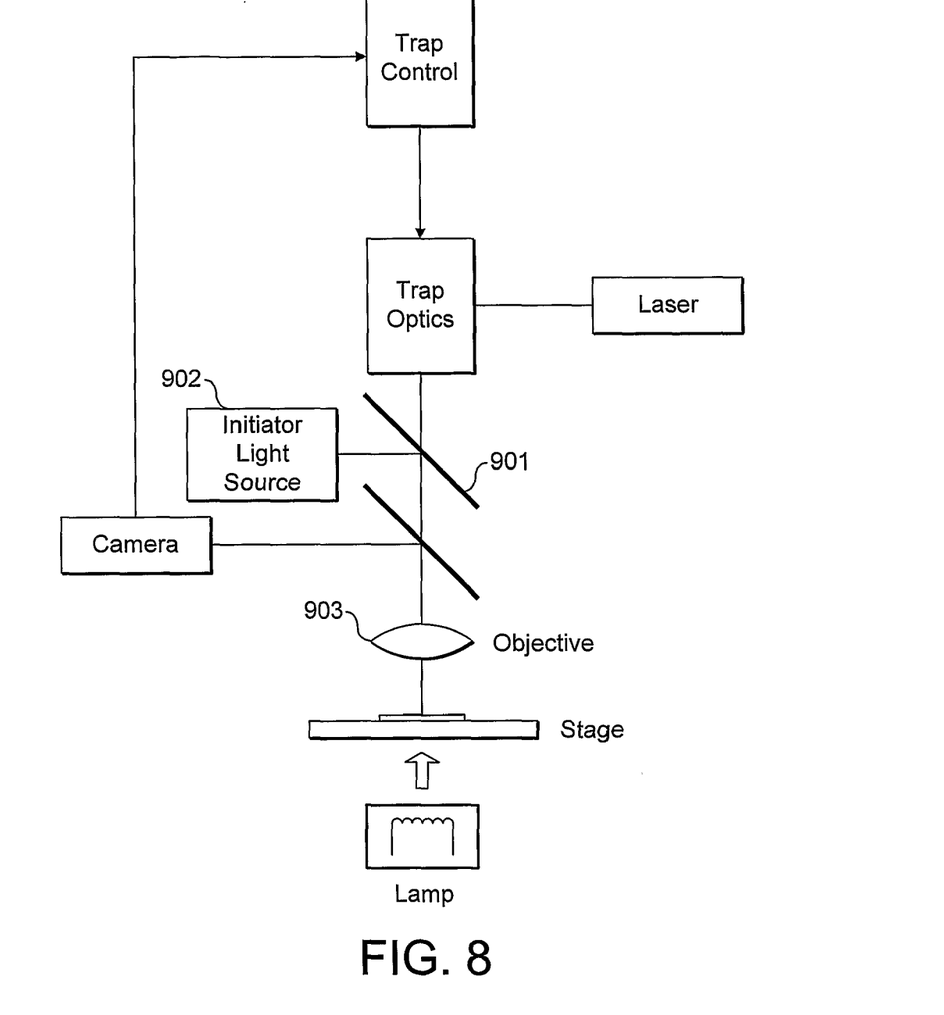
FIG. 8 shows an optical tweezer system modified to include photo-initiator means.

The apparatus shown in FIG. 1 for shaping the droplets may be modified to include means for activating photo-initiators and commencing a polymerisation process. An example of the modified apparatus is shown in FIG. 8. The apparatus is substantially similar to that described in FIG. 1 except for the following additions. An extra beamsplitter 901 and an initiator light source 902 are added. The beamsplitter 901 is placed in the optical trap generating laser beam before the objective 903. The initiator light source provides a beam of light incident on the beamsplitter 901 and is deflected by it to pass through the objective lens.

The objective lens focuses the light from the initiator light source onto the droplet. The whole droplet may be illuminated at once to ensure polymerisation commences throughout the droplet at the same time. Hence, the size of the focussed initiator beam incident on the droplet should be larger than the trap size.

During polymerisation the forces inside the droplet may be large enough to eject the droplet from the optical traps. This can be overcome by increasing the strength of the trapping beams.

Further information on the use of emulsions and microemulsions with monomers to facilitate polymerisation is a described in "Micro-emulsion polymerisation of methyl methacrylate photoinitiated by symmetrical azocompounds of different hydrophobicity", Encinas et al, Langmuir 14 (20), 5691-5694, 1998.

Figure 9:
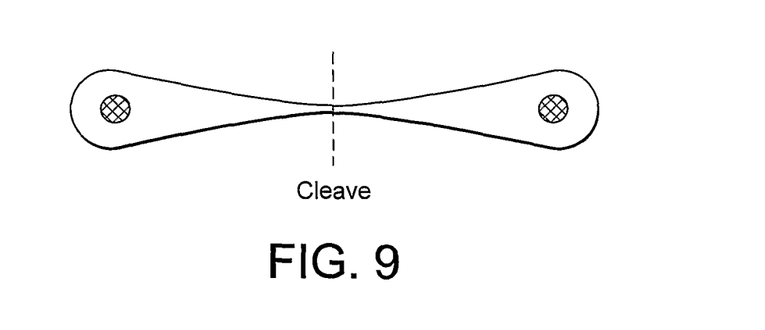
FIG. 9 shows a needle structure formed using two optical traps.

Of course, the shapes that can be produced are not limited to those described above but are any that can be formed using any number of optical traps. A device that may be particularly useful in the medical field might be an ultra fine needle. This could be used for probing cells. Such a device could be formed using two traps as described in FIG. 3. By moving the traps further and further apart as shown in FIG. 10, a dumbbell shape may be achieved. After polymerisation the body may be cleaved at the middle to provide a fine needle. Similarly many other tools for microscopic analysis of cells could be made, and also tools for manipulating or aggregating colloids.

Experiments have demonstrated that it is possible, using the described techniques, to separate a single droplet into two or more smaller droplets, or to pull multiple daughter droplets from a single larger droplet. These droplets remain connected by a thin thread of droplet fluid. We have demonstrated threads with lengths of around 1 to 20 μm, and diameters of about 1~1000 μm. The droplet fluid is able to flow along or thorough the threads, transforming fluid between the droplets. Polymerization of the thread fluid can be effected to form ultrafine structures such as needles and probe tips. Other uses for the deforming droplet are found in microfluidic applications, for example in creating, in situ, solid, shaped valve structures internal to a microfluidic device at a point where only fluids can access, and in lab-on-chip applications for fluid flow.

The solidification of the droplets is not limited to the polymerisation technique described above but may use liquid droplets which by the action of heat, an initiator, or both may solidify the droplet. Alternatively, the liquid may be solidified by rapid freezing.

Other variations to the described embodiments will be apparent to the skilled person.

The invention claimed is:

1. A method of deforming a droplet comprising:
generating a plurality of optical traps;
directing the plurality of optical traps at the droplet; and
moving at least one of the optical traps to deform the shape of the droplet,
wherein the droplet is formed of a first liquid, the droplet being suspended within a second, surrounding liquid, and the interface between the droplet and the surrounding liquid comprises a surfactant to lower the surface tension between the droplet and the surrounding liquid.

2. The method of claim 1 wherein the optical traps are moved relative to each other to deform the shape of the droplet.

3. The method of claim 1 wherein the optical traps are incident within the droplet.

4. The method of claim 1 wherein the optical traps are incident outside the droplet.

5. The method of claim 1 wherein the first liquid and the second liquid form an emulsion.

6. The method of claim 5 wherein the emulsion is an oil-in-water based emulsion.

7. The method of claim 5 wherein the emulsion contains Aerosol OT, heptane and sodium chloride.

8. The method of claim 1 further comprising the step of solidifying the droplet.

9. The method of claim 1 further comprising causing polymerisation of monomers included within the droplet.

10. The method of claim 9 further comprising optically triggering an initiator to cause polymerisation.

11. The method of claim 10 wherein the initiator is included in the droplet.

12. Droplet deformation apparatus comprising:
a sample space for holding at least one droplet formed of a first liquid, the droplet being suspended in a second, surrounding liquid, and the interface between the droplet and the surrounding liquid comprising a surfactant to lower the surface tension between the droplet and the surrounding liquid;
a trap generator arranged to generate a plurality of optical traps incident on the droplet; and
a controller arranged to manipulate the optical traps to deform the droplet.

13. The apparatus of claim 12 further comprising:
imaging apparatus arranged to view the droplet from two or more aspects.

14. The apparatus of claim 12 wherein the first liquid and the second liquid form an emulsion.

15. The apparatus of claim 13 wherein the droplet contains monomers and the droplet or the surrounding liquid contains an initiator.

16. The apparatus of claim 15 wherein the initiator is a photo-initiator.

17. The apparatus of claim 16 further comprising:
a trigger generator arranged to illuminate the droplet and cause polymerisation of the droplet.

18. The apparatus of claim 17 wherein the trigger generator is comprises:
a laser to generate light suitable to activate the photo-initiator; and
optical components arranged to direct the laser light at the droplet.

19. A method of fabricating a shaped polymer particle from an emulsion containing an initiator and droplets containing monomers, comprising:
generating a plurality of optical traps directed at the droplet, wherein the droplet is formed of a first liquid, the droplet being suspended within a second, surrounding liquid, and the interface between the droplet and the surrounding liquid comprises a surfactant to lower the surface tension between the droplet and the surrounding liquid;
moving the optical traps to deform the shape of the droplet; and
initiating polymerisation of the droplet.

20. The method of claim 19 wherein the initiator is a photo-initiator.

21. The method of claim 20 polymerisation is initiated by irradiating the whole droplet simultaneously.

22. The method of claim 19 wherein the droplet contains the monomer styrene and the initiator dibenzyl ketone.

23. The method of claim 19 wherein the droplet contains the monomer methyl methacrylate and the initiator 2,2'-azo-bis(isobutyronitrile).

24. The method of claim 19 wherein the initiator is 2,2'-azobis(2-amidinopropane).

25. A method of deforming a droplet comprising:
generating at least one variable geometry optical trap;
directing the at least one variable geometry optical trap at the droplet; and
adjusting the geometry of the optical trap to deform the droplet,
wherein the droplet is formed of a first liquid, the droplet being suspended within a second, surrounding liquid, and the interface between the droplet and the surrounding liquid comprises a surfactant to lower the surface tension between the droplet and the surrounding liquid.

26. The method of claim 25 wherein the variable geometry optical trap is formed using multiple beams.

27. The method of claim 25 wherein the variable geometry optical trap is incident within the droplet.

28. The method of claim 25 further comprising the step of solidifying the droplet.

29. A method of forming a shaped droplet comprising:
providing a droplet of a first liquid suspended within a second, surrounding liquid, with a surfactant to lower the interfacial surface tension between the droplet and the surrounding second liquid;
forming a plurality of optical traps at the droplet; and
manipulating the optical traps to deform the shape of the droplet.

30. The method of claim 1 wherein the surface tension at the interface between the droplet and the surrounding liquid is less than $1 \times 10^{-4}$ $Nm^{-1}$.

31. The apparatus of claim 12, wherein the surface tension at the interface between the droplet and the surrounding liquid is less than $1 \times 10^{-4}$ $Nm^{-1}$.

32. The method of claim 19, wherein the surface tension at the interface between the droplet and the surrounding fluid liquid is less than $1 \times 10^{-4}$ $Nm^{-1}$.

33. The method of claim 25, wherein the surface tension at the interface between the droplet and the surrounding liquid is less than $1 \times 10^{-4}$ $Nm^{-1}$.

34. The method of claim 29, wherein the surface tension at the interface between the droplet and the surrounding fluid liquid is less than $1 \times 10^{-4}$ $Nm^{-1}$.

35. The method of claim 1, wherein the surfactant lowers the surface tension between the droplet and the surrounding liquid by three orders of magnitude or more.

36. The method of claim 1, wherein the surfactant lowers the surface tension between the droplet and the surrounding liquid to a level which is comparable to an optical trap force.

37. The apparatus of claim 12, Wherein the surfactant lowers the surface tension between the droplet and the surrounding liquid by three orders of magnitude or more.

38. The apparatus of claim 12, wherein the surfactant lowers the surface tension between the droplet and the surrounding liquid to a level which is comparable to an optical trap force.

* * * * *